United States Patent [19]

Jung et al.

[11] Patent Number: 4,547,573
[45] Date of Patent: Oct. 15, 1985

[54] PROCESS FOR PREPARING CEPHALOSPORIN DERIVATIVES

[75] Inventors: Fréderic H. Jung, Rilly la Montagne; Annie A. Olivier, Reims, both of France; Frank Loftus, Macclesfield, England

[73] Assignees: ICI Pharma, Enghien-les-Bains, France; Imperial Chemical Industries PLC, London, England

[21] Appl. No.: 557,585

[22] Filed: Dec. 2, 1983

[51] Int. Cl.$^4$ .................. C07D 501/14; A61K 31/545
[52] U.S. Cl. ........................ 544/27; 544/28; 544/22
[58] Field of Search .............. 544/16, 26, 22, 27, 544/28; 424/246

[56] References Cited

U.S. PATENT DOCUMENTS 4,463,173  7/1984  Jung ........................ 544/22
4,490,382  12/1984  Jung et al. .................. 260/245.2 R

FOREIGN PATENT DOCUMENTS 31708  7/1981  European Pat. Off. .
55562  7/1982  European Pat. Off. .
72608  2/1983  European Pat. Off. .

Primary Examiner—Nicholas S. Rizzo
Attorney, Agent, or Firm—Cushman, Darby & Cushman

[57] ABSTRACT

A process for the manufacture of a cephalosporin derivative of the formula I

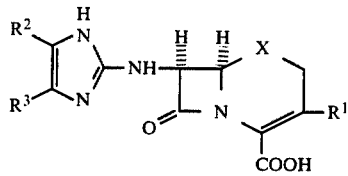

in which X is sulphur, oxygen or sulphinyl; $R^1$ is any one of the C-3 substituents from antibacterially-active cephalosporins known in the art; $R^2$ is hydrogen or 1-6C alkyl; $R^3$ is hydrogen or 1-6C alkyl; and the pharmaceutically-acceptable acid-addition and base-addition salts thereof, characterized by cyclization of a compound of the formula II:

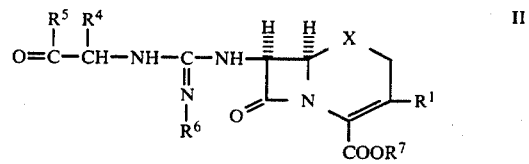

or a derivative thereof in which the carbonyl group is masked, or an acid-addition salt thereof, in which $R^4$ and $R^5$ individually have one of the values for $R^2$ and $R^3$, $R^6$ is a nitrogen-protecting group and $R^7$ is hydrogen or any one of the cephalosporin 3-carboxylic acid protecting groups known in the art;

whereafter when the product from the cyclization retains the protecting group $R^7$ (when $R^7$ is other than hydrogen) the protecting group $R^7$ is replaced by hydrogen by conventional means;

and whereafter when the compound of the formula I is obtained in the form of the free base or salt, and a pharmaceutically-acceptable salt or free base respectively is required, any necessary conversion between free base and salt is carried out by conventional means.

2 Claims, No Drawings

PROCESS FOR PREPARING CEPHALOSPORIN DERIVATIVES

The invention relates to a process for the manufacture of cephalosporin derivatives which have antibacterial properties.

In European Patent Publication Nos. 31708 and 55562 there are described cephalosporin derivatives which have an optionally-substituted imidazol-2-ylamino radical attached at the 7-position of the cephalosporin nucleus. In these publications the preferred method of attaching the imidazole ring is via the reaction of a 7-aminocephalosporin derivative with an optionally-substituted 2-fluoroimidazole. However the preparation of such 2-fluoroimidazoles is difficult and tedious. European Patent Publication No. 72608 describes the preparation of these same derivatives by reaction of a 7-aminocephalosporin with a 2,2-dialkoxycyanamide. The present invention provides a facile alternative synthesis of the required 7-(imidazol-2-yl)amino-cephalosporin derivatives from readily available starting materials. The reaction proceeds in higher yield than those previously obtained, and the purity of the product is also high.

According to the invention there is provided a process for the manufacture of a cephalosporin derivative of the formula I:

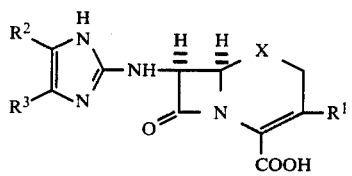

in which

X is sulphur, oxygen or sulphinyl;

$R^1$ is any one of the C-3 substituents from antibacterially-active cephalosporins known in the art;

$R^2$ is hydrogen or 1–6C alkyl;

$R^3$ is hydrogen or 1–6C alkyl;

and the pharmaceutically-acceptable acid-addition and base-addition salts thereof, characterised by cyclisation of a compound of the formula II:

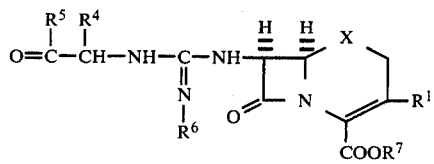

or a derivative thereof in which the carbonyl group is masked, or an acid-addition salt thereof, in which X and $R^1$ have the meanings stated above, $R^4$ and $R^5$ individually have one of the values given above for $R^2$ and $R^3$, $R^6$ is a nitrogen-protecting group and $R^7$ is hydrogen or any one of the cephalosporin 4-carboxylic acid protecting groups known in the art;

whereafter when the product from the cyclisation retains the protecting group $R^7$ (when $R^7$ is other than hydrogen) the protecting group $R^7$ is replaced by hydrogen by conventional means;

and whereafter when the compound of the formula I is obtained in the form of the free base or salt, and a pharmaceutically-acceptable salt or free base respectively is required, any necessary conversion between free base and salt is carried out by conventional means.

It is to be understood that in the above formula I and throughout this specification the illustrated stereochemistry of the cephem nucleus of the formula III:

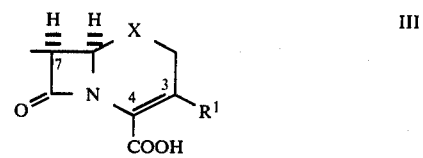

is the absolute configuration. It is also to be understood that when X is sulphinyl, the oxygen may be in the R or S absolute configuration, or a mixture of these two. It is further to be understood that although the double bonds in the imidazole ring have been inserted in particular positions, other tautomeric forms are, in certain instances, possible and these tautomeric forms are included within the scope of this invention. Note however that the delta-3 double bond in the cephalosporin nucleus is fixed in position. When the compound of the formula I is present as the free base, it will generally exist in the form of the zwitterion.

A particular value for $R^1$ is hydrogen, halogen (e.g. fluorine, chlorine or bromine), hydroxy or amino or a saturated or unsaturated, substituted or unsubstituted 1–20C organic group. Illustrative values for $R^1$ when it is a 1–20C organic group are as follows:

(a) 1–6C alkyl, benzyl optionally substituted by fluorine or methoxy, 1–6C haloalkyl, formyl, carboxy, 1–6C alkoxy, 1–6C alkylthio, 1–6C alkylamino, phenylamino, benzylamino, 3–6C cycloalkylamino, cyano, 2–6C alkoxycarbonyl, 2–6C alkanoyl, 3–10C alkoxycarbonylalkyl, 2–6C alkoxycarbonylamino, 2–6C alkylthiocarbonylamino, piperidino, pyrrolidino, morpholino, 2–6C alkanoylamino, ureido, 2–6C alkylureido, 3–8C dialkylureido, 1–6C alkanesulphinyl, 1–6C alkanesulphonyl, heterocyclyl and heterocyclylthio in which the heterocycle is a 1,3,4-thiadiazol-2-yl or 1,3,4-oxadiazol-2-yl, each optionally substituted in the 5-position, a 1H-tetrazol-5-yl optionally substituted in the 1-position, or a 1H-1,2,3-triazol-4-yl optionally substituted in the 1- or 5-position, the optional substituents in each of these heterocycles being 1–6C alkyl, 1–6C sulphoalkyl, 2–6C carboxyalkyl, 1–6C haloalkyl or 3–6C alkylthioalkyl, or pyridazin-3-yl, oxazol-3-yl or thiazol-3-yl each optionally substituted by 1 or 2 radicals selected from 1–6C alkyl, 1–6C haloalkyl and 2–6C alkoxycarbonyl;

(b) radicals of the formula IV:

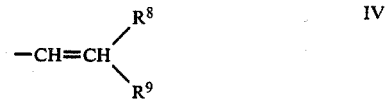

in which $R^8$ and $R^9$, same or different, are hydrogen, 1–6C alkyl, 5–7C cycloaliphatic, phenyl, phenyl(1–6-C)alkyl (e.g. benzyl, 2-phenylethyl), formyl, cyano, carboxy, 2–6C alkoxycarbonyl, sulpho, 1–6C alkanesulphinyl, 1–6C alkanesulphonyl, 1–6C alkoxy, 1–6C alkylthio, carbamoyl, nitro, 1–6C hydroxyalkyl, methylcarbamoyloxymethyl, benzylcarbamoyloxymethyl, 2–6C alkoxymethyl, 2–6C alkylthiomethyl, 2-haloethoxymethyl, cyclopentyloxymethyl, benzyloxymethyl or 3–8C alkanoyloxymethyl or of the formula $CH_2SHet^1$ in which Het[1] is 1,3,4-thiadiazol-2-yl or 1,3,4-oxadiazol-2-yl, both optionally substituted in the 5-position by methyl, 1H-triazol-5-yl optionally substituted in the 1-position by methyl or 1H-1,2,3-triazol-4-yl;

(c) radicals of the formula V:

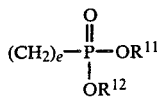

V in which $R^{10}$ is cyano, carboxy or 2-6C alkoxycarbonyl;

(d) radicals of the formula VI:

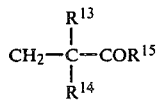

VI in which $R^{11}$ and $R^{12}$, same or different, are hydrogen or 1-6C alkyl and e is 1 to 4;

(e) radicals of the formula CH$_2$Y in which Y is an atom or group which is the residue of a nucleophile or a derivative of a residue of a nucleophile, such a nucleophile or a derivative thereof being:

A. 3-15C trialkylamines;

B. heterocyclic amines having more than one heteroatom, at least one heteroatom being nitrogen;

C. pyridines which are optionally substituted by 1 to 3 substituents selected from halogen, 1-6C alkyl, phenyl, benzyl, 2-10C alkoxyalkyl, 3-10C alkanoyloxymethyl, formyl, carbamoyl, 2-6C alkanoyloxy, 2-6C alkoxycarbonyl, 1-6C alkoxy, phenoxy, benzyloxy, 1-6C alkylthio, phenylthio, benzylthio, cyano, hydroxy, 2-6C alkylcarbamoyl, 3-10C dialkylcarbamoyl, 2-6C (hydroxyalkyl)carbamoyl and 2-6C carbamoylalkyl;

D. azide;

E. amino, 1-6C alkanoylamino and benzoylamino;

F. cyanide, pyrroles and substituted pyrroles;

G. nucleophiles giving rise to $R^1$ of the formula VII:

$$CH_2-\overset{R^{13}}{\underset{R^{14}}{C}}-COR^{15}$$

VII in which $R^{13}$ and $R^{14}$, same or different, are selected from hydrogen, cyano, 1-6C alkyl, 2-6C alkoxycarbonyl, mono- or di-phenyl(1-6C)alkoxycarbonyl, 2-6C alkanoyl, phenyl(1-6C)alkyl, cyclopentyl and cyclohexyl, and phenyl optionally substituted by 1 or 2 radicals selected from halogen, 1-6C alkyl, 1-6C alkoxy, 1-6C alkylamino, nitro and amino, and $R^{15}$ is selected from hydrogen, 1-6C alkyl, phenyl(1-6C)alkyl, cyclopentyl and cyclohexyl, and phenyl optionally substituted by 1 or 2 radicals selected from halogen, 1-6C alkyl, 1-6C alkoxy and 1-6C alkylamino;

H. thiourea optionally substituted by 1-6C alkyl, phenyl or 5-7C alicyclyl, dithiocarbamates, thioamides substituted by 1-6C alkyl or phenyl or thiosemicarbazides, thiosulphates, or phenylthioacids and dithioacids of the formula VIII:

VIII in which $R^{16}$ and $R^{17}$, same or different, are hydrogen, 1-6C alkyl, 2-6C hydroxyalkyl, 3-8C alkylaminoalkyl, 4-10C dialkylaminoalkyl or phenyl, or $R^{16}$ and $R^{17}$ are joined to form a pyrrolidine, piperidine or morpholine ring, or a piperazine ring which is optionally substituted on nitrogen by one or two (in quaternised form) radicals selected from 1-6C alkyl and 3-6C alkenyl;

I. compounds of the formula $R^{18}S(O)_dH$ in which d is 0, 1 or 2 and $R^{18}$ is 1-6C alkyl, 5-7C alicyclic, phenyl optionally substituted by carboxy, or phenyl(1-6C)alkyl or a 5- or 6-membered heterocyclic ring (partially or fully unsaturated) containing 1 to 4 nitrogens which ring may further include (where possible) oxygen and/or sulphur, in which the nitrogen may be in the oxide form, which heterocyclic ring may be fused with another heterocyclic ring within the same definition or may be fused with a benzene ring, the above phenyl, phenylalkyl, heterocyclic or fused benzene ring being optionally substituted (where possible) by 1 or 2 substituents selected from halogen, 1-6C alkyl, 1-6C haloalkyl, phenyl, 2-6C alkenyl, 1-6C alkoxy, oxo, hydroxy, mercapto, amino, carboxy, cyano, isothiocyanate, carbamoyl, sulphamoyl, 2-6C alkoxycarbonyl, 3-6C alkenyloxycarbonyl, phenyl(1-6C)-alkylcarbonyl, phenoxycarbonyl, 2-6C hydroxyalkyl, 3-6C dihydroxyalkyl, sulphoamino and 1-6C alkanesulphonylamino and radicals of the formula B—$R^{19}$ in which B is a 2-8C straight or branched chain which may be interrupted by sulphur, oxygen, NH or 1-6C N-alkyl and $R^{19}$ is selected from hydroxy, mercapto, cyano, 1-6C alkylamino, 2-6C dialkylamino, 2-6C alkanoylamino, carboxy, sulpho, carbamoyl, sulphamoyl, amidino, guanidino, 2-6C alkoxycarbonyl, 2-6C alkylcarbamoyl, 2-6C dialkylcarbamoyl, 1-6C alkylsulphamoyl, 2-6C dialkylsulphamoyl, sulphoamino, ureido, 1-6C alkoxy, 1-6C alkylthio, 1-6C alkanesulphonyl, 2-6C alkanoyl, and 2-6C alkanoyloxy and radicals of the formula —B—$R^{20}$ in which $R^{20}$ is 1-6C alkyl or of the formula B—$R^{19}$ in which B and $R^{19}$ have the meanings given above and radicals of the formula $NR^{21}R^{22}$ in which $R^{21}$ and $R^{22}$, same or different, are selected from 1-6C alkyl, groups of the formula B—$R^{19}$ in which B and $R^{19}$ have the definitions given above, 1-6C alkoxycarbonyl, 2-6C alkanoyl, carbamoyl, 2-6C alkylcarbamoyl and 3-10C dialkylcarbamoyl;

J. radicals of the formula $R^{23}$—OH in which $R^{23}$ is hydrogen, 1-6C alkyl, 3-6C alkenyl, 3-6C alkynyl, 5-7C cycloalkyl, 6-12C cycloalkylalkyl, phenyl, phenyl(1-6C)alkyl or furfuryl, any of which may be substituted by 1 or 2 radicals selected from halogen, 1-6C alkyl, nitro, hydroxy, carboxy, 2-6C alkanoyloxy, 2-6C alkoxycarbonyl, 2-6C alkanoyl, 1-6C alkanesulphonyl, 1-6C alkoxysulphonyl, amino, 1-6C alkylamino and 2-6C alkanoylamino or $R^{23}$ is carbamoyl;

K. radicals of the formula $R^{24}$—Q—COOH in which Q is a direct bond, oxygen, sulphur or NH and $R^{24}$ is:

(i) hydrogen or 1-6C alkyl which may be interrupted by oxygen, sulphur or NH and/or substituted by cyano, carboxy, methoxycarbonyl, ethoxycarbonyl, hydroxy, carboxycarbonyl, amino or halogen;

(ii) 2-6C alkenyl which may be interrupted by oxygen, sulphur or NH;

(iii) phenyl, hydroxyphenyl, chlorophenyl, fluorophenyl, tolyl, nitrophenyl, aminophenyl, methoxyphenyl, methylthiophenyl, thienyl, pyridyl, cyclohexyl, cyclopentyl, sydnonyl, naphthyl or ethoxynaphthyl; or (iv) $R^{25}$—$(CH_2)_g$ where $R^{25}$ has the value for $R^{24}$ listed in (i) above and g is 1 to 4; and (f) radicals of the formula IX:

  IX in which $R^{26}$ is (1) 1–6C alkyl (e.g. methyl), L2-amino-2-carboxyethyl or phenyl;

(2) pyridyl or the N-oxide thereof;

(3) pyridazin-3-yl substituted in the 6-position by 1–6C alkyl (e.g. methyl), methoxy, amino or 1–6C acylamino (e.g. acetylamino), or the N-oxide thereof, or pyrimidin-2-yl or tetrazolo[4,5-b]pyridazin-6-yl;

(4) 5,6-dioxo-1,4,5,6-tetrahydro-1,2,4-triazin-3-yl substituted in the 4-position; 1,3,4-triazol-5-yl or 2-alkoxycarbonyl-1,3,4-triazol-5-yl in which the alkoxycarbonyl is 2–6C (e.g. methoxycarbonyl), each substituted in the 1-position:

(a) by 1–6C alkyl (e.g. methyl) optionally substituted by 1–6C alkoxy (e.g. methoxy), 1–6C alkylthio (e.g. methylthio), phenyl, formyl, carbamoyl, 2–6C alkylcarbamoyl (e.g. methylcarbamoyl), 3–10C dialkylcarbamoyl (e.g. dimthylcarbamoyl), 1–6C alkanoyl (e.g. acetyl), 2–6C alkoxycarbonyl (e.g. methoxycarbonyl) or thiazolidin-2-yl;

(b) by allyl, 2,3-dihydroxypropyl, 1,3-dihydroxyprop-2-yl, 2-formyl-2-hydroxyethyl, 3-formyloxy-2-hydroxypropyl, 2,3-bisformyloxypropyl or 1,3-bisformyloxyprop-2-yl;

(c) by 2–4C alkyl which is substituted by hydroxy, carbamoyloxy, 1–6C alkanoyl (e.g. acetyl) (which can itself be optionally substituted by amino, 1–6C alkylamino [e.g. methylamino] or 2–10C dialkylamino [e.g. dimethylamino]), 1–6C alkanesulphinyl (e.g. methanesulphinyl), 1–6C alkanesulphonyl (e.g. methanesulphonyl), amino, 1–6C alkylamino (e.g. methylamino), 2–10C dialkylamino (e.g. dimethylamino), sulphoamino, 1–6C alkanesulphonylamino (e.g. methanesulphonylamino), sulphamoylamino, 1–6C alkanoylamino (e.g. acetylamino) (which can itself be optionally substituted by a hydroxy, amino, 1–6C alkylamino [e.g. methylamino] or 2–10C dialkylamino [e.g. dimethylamino]), 2–6C alkoxycarbonylamino (e.g. methoxycarbonylamino), ureido, 2–6C alkylureido (e.g. methylureido) or 3–10C dialkylureido (e.g. dimethylureido);

(d) by a radical of the formula X, XI or XII:

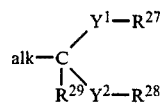  X

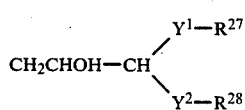  XI

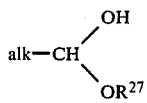  XII in which alk is 1–4C alkylene (e.g. ethylene), $Y^1$ and $Y^2$ are the same and are oxygen or sulphur and $R^{27}$ and $R^{28}$ are the same and are 1–6C alkyl (e.g. methyl) or $Y^1$ and $Y^2$ are the same or different and are oxygen or sulphur and $R^{27}$ and $R^{28}$ are joined to form 2–3C alkylene, and $R^{29}$ is hydrogen or 1–3C alkyl (e.g. methyl);

(e) by 1–6C (e.g. methyl) substituted by 1–6C alkyl (e.g. methyl) substituted by 1–6C alkoxyimino (e.g. methoxyimino) or hydroxyimino;

(5) 1,4-diallkyl-5,6-dioxo-1,4,5,6-tetrahydro-1,2,4-triazin-3-yl, 1-alkyl-5,6-dioxo-1,4,5,6-tetrahydro-1,2,4-triazin-3-yl or 2-alkyl-5,6-dioxo-1,2,5,6-tetrahydro-1,2,4-triazin-3-yl in each of which the alkyl is 1–6C (e.g. methyl);

(6) 1,3,4-triazol-5-yl, 1,2,3-triazol-5-yl or 1-alkyl-1,2,4-triazol-5-yl in which the alkyl is 1–6C (e.g. methyl) which is optionally substituted in the 3-position by 2–6C alkoxycarbonyl (e.g. methoxycarbonyl);

(7)a. 1,3,4-thiadiazol-5-yl optionally substituted by 1–6C alkyl (e.g. methyl), trifluoromethyl, 1–6C alkoxy (e.g. methoxy), 1–6C alkylthio (e.g. methylthio), 2–4C hydroxyalkylthio (e.g. 2-hydroxyethylthio), 1–6C alkanesulphonyl (e.g. methanesulphonyl), hydroxy, 1–6C hydroxyalkyl (e.g. hydroxymethyl), carboxy, 2–6C carboxyalkyl (e.g. carboxymethyl), amino, 1–6C alkylamino (e.g. methylamino), 2–10C dialkylamino (e.g. dimethylamino), 1–6C aminoalkyl (e.g. 2-aminoethyl), 2–8C alkylaminoalkyl (e.g. 2-methylaminoethyl), 3–12C dialkylaminoalkyl (e.g. 2-dimethylaminoethyl), 1–6C alkanoylamino (e.g. acetylamino) or 2–8C alkanoylaminoalkyl (e.g. acetylaminoethyl), or b. 1,2,4-thiadiazol-5-yl substituted by 1–6C alkyl (e.g. methyl) or 1–6C alkoxy (e.g. methyl);

(8)a. 1,3,4-oxadiazol-5-yl optionally substituted by 1–6C alkyl (e.g. methyl), trifluoromethyl, phenyl, 1–6C aminoalkyl (e.g. aminomethyl), 2–8C alkylaminoalkyl (e.g. methylaminomethyl), 3–10C dialkylaminoalkyl (e.g. 2-dimethylaminoethyl) or 2–8C alkanoylaminoalkyl (e.g. acetylaminomethyl) or b. oxazol-2-yl optionally substituted in the 4-position by 1–6C alkyl (e.g. methyl);

(9) tetrazol-5-yl radical optionally substituted in the 1-position by:

(a) 1–6C alkyl (e.g. methyl) itself optionally substituted by 1–6C alkoxy (e.g. methoxy), sulpho, carboxy, formyl or sulphamoyl;

(b) 2–4C alkyl (e.g. ethyl) substituted by hydroxy, amino, 1–6C alkylamino (e.g. methylamino), 2–8C dialkylamino (e.g. dimethylamino), 1–6C alkanoylamino (e.g. acetylamino), 2–6C carboxyalkylamino (e.g. carboxymethylamino), sulphamoylamino, sulphoamino, ureido, 2–6C alkylureido (e.g. methylureido) or 3–8C dialkylureido (e.g. dimethylureido);

(c) 1–6C alkyl (e.g. ethyl) substituted by hydroxyimino or 1–6C alkoxyimino (e.g. methoxyimino);

(d) phenyl, 2,3-dihydroxypropyl, 1,3-dihydroxyprop-2-yl, 2-formyl-2-hydroxyethyl, 3-formyloxy-2-hydroxypropyl, 2,3-bisformyloxypropyl or 1,3-bisformyloxy-2-propyl; or (e) a radical of the formula X above in which $R^{29}$ is a hydrogen, or a radical of the formula XI above, in both of which $Y^1$, $Y^2$, $R^{27}$ and $R^{28}$ are as given above.

A particular value for $R^2$ or $R^3$ is hydrogen or methyl.

A particular acid-addition salt of the cephalosporin derivative manufactured by the process of the invention is, for example, a salt formed with hydrochloric, hydrobromic, phosphoric, sulphuric, citric or maleic acid. A suitable base-addition salt of the cephalosporin derivative manufactured by the process of the invention is, for example, an alkali metal salt (e.g. a sodium or potassium salt), an alkaline earth metal salt (e.g. a calcium or magnesium salt), or a salt with a primary, secondary or tertiary organic amine (e.g. triethylamine, procaine, dibenzylamine and N,N$^1$-dibenzylethylenediamine, and other amines which have been used to form salts with cephalosporins).

A preferred group of compounds which may be prepared by the process of the invention are those of the formula I in which X is sulphur, $R^2$ and $R^3$ are hydrogen and $R^1$ is hydrogen, chlorine, methyl, acetoxymethyl, methoxymethyl, hydroxymethyl, azidomethyl, aminomethyl, benzoyloxymethyl, acetylaminomethyl, carbamoyloxymethyl or 2-(1-methyltetrazol-5-ylthio)-trans-vinyl or of the formula $CH_2S(O)_d$—$R^{18}$ in which d and $R^{18}$ have the meanings given above. In particular $CH_2S(O)_d$—$R^{18}$ may represent 1-methyl-1H-tetrazol-5-ylthiomethyl, 1-carboxymethyl-1H-tetrazol-5-ylthiomethyl, 1-(2-dimethylamino)ethyl-1H-tetrazol-5-ylthiomethyl, 1-sulphomethyl-1H-tetrazol-5-ylthiomethyl, 1-isopropyl-1H-tetrazol-5-ylthiomethyl, 1-(2,2,2-trifluoro)ethyl-1H-tetrazol-5-ylthiomethyl, 1-phenyl-1H-tetrazol-5-ylthiomethyl, 1-(2-methylthio)ethyl-1H-tetrazol-5-ylthiomethyl, 1,3,4-thiadiazol-2-ylthiomethyl, 5-methyl-1,3,4-thiadiazol-2-ylthiomethyl, 1,2,3-thiadiazol-5-ylthiomethyl, 1H-1,2,3-triazol-4-ylthiomethyl, 5-trifluoromethyl-1H-1,2,4-triazol-3-ylthiomethyl, 4,6-dimethylpyrimid-2-ylthiomethyl, 2-thiazolin-2-ylthiomethyl, benzoxazol-2-ylthiomethyl, benzthiazol-2-ylthiomethyl, 2-carboxyphenylthiomethyl, (6-carboxymethyl-7-hydroxypyrrolo[1,2-b]pyridazin-2-yl)thiomethyl, 2-methylthio-1,3,4-thiadiazol-5-ylthiomethyl, 2-mercapto-1,3,4-thiadiazol-5-ylthiomethyl, 2-acetylamino-1,3,4-thiadiazol-5-ylthiomethyl, 5-methyl-1,2,4-thiadiazol-2-ylthiomethyl, 2-sulphomethyl-1,2,4-oxadiazol-5-ylthiomethyl, 4-methyl-5-(3-carboxypropyl)thiazol-2-ylthiomethyl, 2H-2-methyl-1,2,3-triazol-4-ylthiomethyl, 1H-1,2,4-triazol-2-ylthiomethyl, 4,5-dihydro-6-hydroxy-4-methyl-5-oxo-1,2,4-triazin-3-ylthiomethyl, 2,5-dihydro-6-hydroxy-2-methyl-5-oxo-1,2,4-triazin-3-ylthiomethyl, 1-oxidopyrid-2-ylthiomethyl, imidazo[4,5-b]pyrid-2-ylthiomethyl or imidazo[4,5-d]pyrimidin-2-ylthiomethyl.

Particularly preferred compounds which may be manufactured by the process of the invention are those of the formula I in which X is sulphur, $R^2$ and $R^3$ are hydrogen and $R^1$ is 1H-1,2,3-triazol-4-ylthiomethyl or acetoxymethyl.

A particular value for $R^6$ is, for example, a radical of the formula $SiR^{30}R^{31}R^{32}$ or $CH_2OSiR^{30}R^{31}R^{32}$ in which $R^{30}$, $R^{31}$, $R^{32}$, same or different, are selected from 1-6C alkyl (e.g. methyl, t-butyl), phenyl, phenyl(1-6C)alkyl (e.g. benzyl), of the formula $CH_2OR^{33}$ in which $R^{33}$ is 1-6C alkyl (e.g. methyl) or 3-10C alkoxyalkyl (e.g. 2-methoxyethyl), of the formula $COOR^{34}$ in which $R^{34}$ is 1-6C alkyl or $SiR^{30}R^{31}R^{32}$ in which $R^{30}$, $R^{31}$ and $R^{32}$ have the meanings given above, of the formula $CH_2OCOOR^{35}$ in which $R^{35}$ is 1-6C alkyl (e.g. methyl, t-butyl) or phenyl(1-6C)alkyl (e.g. benzyl), or $R^6$ is triphenylmethyl, tetrahydropyran-2-yl, tetrahydropyran-2-yloxymethyl, toluene-p-sulphonylmethyl or optionally substituted benzyl (e.g. when the substituent is 2,4-dimethoxy or 4-nitro).

A particular value for $R^7$ when it is other than hydrogen is t-butyl, diphenylmethyl or p-methoxybenzyl (replaceable by hydrogen using an acid such as formic or trifluoroacetic acid), benzyl or substituted benzyl, for example p-nitrobenzyl (replaceable by hydrogen by hydrogenolysis) or 2,2,2-trichloroethyl (replaceable by hydrogen using zinc/acetic acid). Alternatively $R^7$ may be a more labile protecting group which is replaced by hydrogen during the course of the process of the invention, thus avoiding the need for a separate deprotection process.

Examples of such more labile protecting groups are trisubstituted silyl in which the substituents are selected from 1-6C alkyl (e.g. methyl, t-butyl), phenyl and substituted phenyl, and those radicals used in the art to act as biological precursors for the 4-carboxy radical in cephalosporins (e.g. labile esters). A particular value for such an art-recognised radical is one of the formula XIII to XXIV inclusive:

| | |
|---|---|
| —CHR$^{36}$OCOR$^{37}$ | XIII |
| —CHR$^{36}$SCOR$^{37}$ | XIV |
| —CHR$^{36}$COR$^{37}$ | XV |
| —CHR$^{36}$OR$^{37}$ | XVI |
| —COOR$^{37}$ | XVII |
| —CHR$^{36}$OCOOR$^{37}$ | XVIII |

XIX

| | |
|---|---|
| —CHR$^{36}$OCH$_2$CH$_2$OCH$_3$ | XX |
| —CH$_2$OCO(CH$_2$)$_t$—CHR$^{38}$—NH$_2$ | XXI |

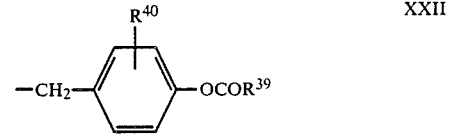

XXII

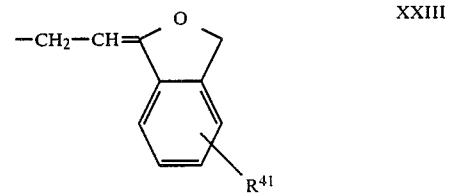

XXIII

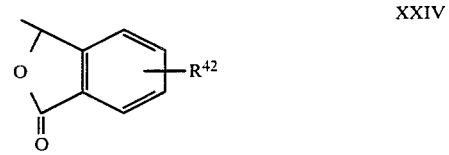

XXIV in which $R^{36}$ is hydrogen or 1-6C alkyl, $R^{37}$ is 1-6C alkyl, $R^{38}$ is hydrogen, 1-6C alkyl, phenyl(1-6C)alkyl or 2-6C alkoxycarbonyl, t is 0 or 1, $R^{39}$ is 1-6C alkyl, phenyl or phenyl(1-6C)alkyl, $R^{40}$ is hydrogen or one, two or three radicals selected from halogen, nitro, cyano, 1-6C alkyl, 1-6C alkoxy, 1-6C alkylthio, 1-6C alkylsulphinyl, 1-6C alkanesulphonyl, 2-6C alkoxycarbonyl, 2-6C alkoxythiocarbonyl, 2-6C alkanoylamino, phenyl, phenoxy, phenylthio, phenylsulphinyl, phenylsulphonyl, phenoxycarbonyl, phenylthiocarbonyl and phenoxythiocarbonyl, $R^{41}$ is hydrogen or one of the values for $R^{39}$ given above and $R^{42}$ is hydrogen or one, two or three radicals selected from halogen, 1-6C alkyl and 1-6C alkoxy.

A preferred value for both $R^6$ and $R^7$ is trialkylsilyl, particularly trimethylsilyl.

A particular masked derivative of the compound of the formula II is one of the formula XXV:

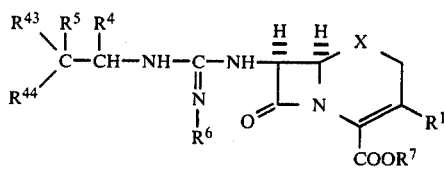

XXV in which X, $R^1$, $R^4$, $R^5$, $R^6$ and $R^7$ have the values given above and in which $R^{43}$ and $R^{44}$, same or different, are hydroxy, cyano or of the formula $NR^{45}R^{46}$ [in which $R^{45}$ and $R^{46}$ are 1–6C alkyl (e.g. methyl), or phenyl or are joined to form a ring] or of the formula $OSiR^{47}R^{48}R^{49}$ [in which $R^{47}$, $R^{48}$ and $R^{49}$, same or differrent, are 1–6C alkyl (e.g. methyl, t-butyl), phenyl(-1–6C)alkyl, (e.g. benzyl) or phenyl] or $R^{43}$ and $R^{44}$ together are of the formula $R^{50}$—ON═ [in which $R^{50}$ is 1–6 C alkyl (e.g. methyl) or hydroxy] or of the formula $R^{51}R^{52}NN═$ [in which $R^{51}$ and $R^{52}$ are 1–6C alkyl (e.g. methyl) or phenyl], or $R^{43}$ is hydrogen and $R^{44}$ is nitro, or $R^{43}$ and $R^{44}$ are of the formula A—$R^{53}$ and B—$R^{54}$ respectively in which A and B are oxygen, sulphur, sulphinyl or NH and $R^{53}$ and $R^{54}$ are joined to form an ethylene or propylene chain which is optionally substituted by one or two 1–6C alkyls (e.g. methyls), or when A and B are oxygen, sulphur or sulphinyl, $R^{53}$ and $R^{54}$, same or different, are 1–6C alkyl (e.g. methyl, ethyl, isopropyl), 1–6C alkanoyl, phenyl, or phenyl(1–6C)alkyl, (e.g. benzyl). Other carbonyl masking groups are described in "Protecting Groups in Organic Chemistry", by T W Greene, John Wiley and Sons, New York, 1981, pages 114–151. A preferred value for both $R^{43}$ and $R^{44}$ is ethoxy.

The process is conveniently carried out in a diluent or solvent such as acetonitrile, methylene chloride, methylene chloride/acetonitrile, acetone or formic acid, and in the presence of an acid catalyst. The acid catalyst may be an aqueous one such as aqueous hydrochloric acid or aqueous hydrofluoric acid. Alternatively, it may be a non aqueous acid catalyst such as boron trifluoride. This latter catalyst is conveniently used in the form of a complex, for example with diethyl ether or acetic acid. In some circumstances it may first be necessary to replace $R^7$ by hydrogen and/or remove the carbonyl masking group (when present) before the cyclisation is carried out. The methods used to replace $R^7$ by hydrogen and/or remove the carbonyl masking group will depend on the nature of the groups involved and will be well known to the skilled chemist. The process of the invention may be carried out over the temperature range $-20°$ to $60°$ C., the preferred temperature range being $0°$ C. to ambient temperature.

Depending on the nature of $R^1$, $R^2$, $R^3$ and $R^6$ it is sometimes possible to identify and even isolate certain products which are intermediates in the chemical process leading from the compound of the formula II to the compound of the formula I. These intermediates are of the formulae XXVI, XXVII and XXVIII:

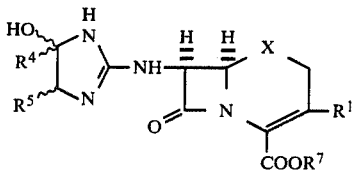

XXVI

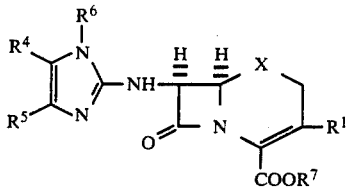

XXVII

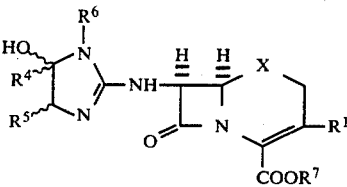

XXVIII and, where the carbonyl masking group is of the formula A—$R^{53}$ or B—$R^{64}$ in which $R^{53}$ and $R^{44}$ are not joined, the corresponding derivatives which carry A—$R^{43}$ or B-$R^{54}$ in place of the hydroxy radical. Generally speaking the intermediate of the formula XXVI is relatively unstable and can be readily transformed into the compound of the formula I. The compounds of the formulae XXVII and XXVIII may be more stable and may in some instances require further treatment to convert them to the compound of the formula I. Thus the compound of the formula XXVIII may require heating in a solvent such as dimethylformamide, or treatment with trifluoroacetic anhydride, and the compound of the formula XXVII may require treatment with trifluoroacetic anhydride. The compounds of the formulae II and XXV in which $R^6$ is hydrogen may also be transient intermediates.

The starting material of the formula II for use in the process may be prepared by reaction of a compound of the formula XXIX:

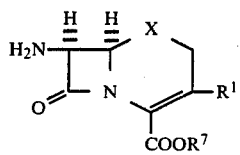

XXIX (itself well known in cephalosporin chemistry) with a compound of the formula XXX:

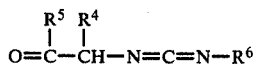

XXX or a derivative thereof in which the carbonyl group adjacent to $R^5$ is masked, in the presence of an acid such as toluene-p-sulphonic, methanesulphonic, trifluoromethanesulphonic, sulphuric or hydrochloric acid and in an organic solvent such as methylene chloride or acetonitrile. Such a carbodiimide may, for example be prepared by oxidation of the corresponding thiourea (made by standard methods) with mercuric oxide (for example as illustrated in Examples 7 and 8) or, when $R^6$ is a silyl derivative, by reaction of the corresponding cyanamide (made by standard methods) with the appropriate silyl chloride (for example as illustrated in Examples 1 and 2).

When $R^7$ in the compound of the formula XXIX is trialkylsilyl and is prepared by silylation of the corresponding free acid, silylation of the 7-amino group may also occur. This 7-substituent may be carried through to form the 7-trialkylsilyl derivative of the compound of the formula II, which is then cyclised in accordance with the process of the invention.

The process of the invention is illustrated, but not limited, by the following Examples. The yields quoted are to be regarded as illustrative rather than limiting. The n.m.r. spectra are quoted in delta relative to tetramethylsilane (delta=0) as internal standard (s=singlet, d=doublet, t=triplet, q=quartet, m=multiplet, br=broad). The temperatures are in degrees Centigrade and the following contractions are used:

HOAc—acetic acid
DMSO—dimethylsulphoxide
THF—tetrahydrofuran
TFA—trifluoroacetic acid
ether—diethyl ether
MeOH—methanol
EtOH—ethanol

EXAMPLE 1

To a suspension of 7-amino-3-(1H-1,2,3-triazol-4-yl)thiomethylceph-3-em-4-carboxylic acid (purity 90%; 157 mg.) in $CH_2Cl_2$ (5 ml.) was added N-trimethylsilyl-1-trimethylsilyloxyvinylamine (244 μl; 2 equivalents) and the mixture was stirred at room temperature for 12 hours to give a clear solution of the trimethylsilyl ester. To this solution was added 1-(2,2-diethoxyethyl)-3-trimethylsilylcarbodiimide (130 mg.), then a solution of trifuloromethanesulphonic acid (45 μl) in $CH_2Cl_2$ (1 ml.) and the mixture was stirred for five minutes at room temperature and then evaporated to dryness. The residue, trimethylsilyl 7-[2-(2,2-diethoxyethyl)-3-trimethylsilyl]guanidino-3-(1H-1,2,3-triazol-4-yl)-thiomethylceph-3-em-4-carboxylate, was dissolved in acetonitrile (10 ml.) and to this solution was added 12N aqueous HCl (120 μl.) and water (400 μl.). After 4 hors at ambient temperature the mixture contained both the corresponding 7-(4-hydroxyimidazolin-2-yl)amino- and 7-(imidazol-2-yl)amino-cephalosporin derivatives. The pH of the mixture was adjusted to 4 with 2N aqueous NaOH and the mixture allowed to stand at room temperature for 18 hours. The solvent was evaporated to dryness to give a brown powder (358 mg.) containing 16% of the required 7-(imidazol-2-yl)amino-3-(1H-1,2,3-triazol-4-yl)thiomethylceph-3-em-4-carboxylic acid (yield from 7-amino derivative 33%). The crude product was purified by chromatography on "Dowex" 1 resin ("Dowex" is a Trade Mark) using 0.5% v/v aqueous HOAc as eluant. The product had the following n.m.r. in $d_6DMSO$: 3.4 (d, 1H); 3.8 (d, 1H); 4.2 (d, 1H); 4.5 (d, 1H); 5.1 (d, 1H); 5.5 (dd, 1H); 6.9 (s, 2H); 7.9 (s, 1H); 9.3 (d, 1H).

The 1-(2,2-diethoxyethyl)-3-trimethylsilylcarbodiimide used as starting material may be prepared as follows:

A solution of cyanogen bromide (2.12 g.), in ether (20 ml.) was added dropwise over 35 minutes to a stirred ice-cooled solution of 2,2-diethoxyethylamine (5.32 g.) in ether (20 ml.). During this addition a white precipitate was formed. The resulting suspension was stirred at 0° for a further hour, filtered and the filtrate evaporated to dryness under reduced pressure to give 2,2-diethoxyethylcyanamide (3.47 g.) as a colourless oily liquid having the following n.m.r. spectrum in $CDCl_3$: 1.24 (t, 6H); 3.1 (d, 2H); 3.65 (m, 4H); 4.0 (br s, 1H); 4.57 (t, 1H).

To a solution of 2,2-diethoxyethylcyanamide (5.5 g.) in anhydrous THF (100 ml.) at 0° was added triethylamine (6.29 ml.) and trimethylsilyl chloride (5.73 ml.). The reaction mixture was stirred at room temperature for 3 hours, the precipitated triethylamine hydrochloride removed by filtration under nitrogen and the filtrate concentrated. The residue was taken up in $CCl_4$, the solvent evaporated and the residue was distilled at 80°/0.2 mm to give 1-(2,2-diethoxyethyl)-3-trimethylsilylcarbodiimide (6.5 g.) having the following n.m.r. in $CDCl_3$: 0.219 (s, 9H); 1.244 (t, 6H); 3.256 (d, 2H); 3.486–3.798 (m, 4H); 4.55 (t, 1H).

EXAMPLE 2

To a mixture of t-butyl 3-acetoxymethyl-7-aminoceph-3-em-4-carboxylate (3.3 g.) and 1-(2,2-diethoxyethyl)-3-t-butyldimethylsilylcarbodiimide (2.0 g.) in $CH_2Cl_2$ (50 ml.) at room temperature was added trifluoromethanesulphonic acid (0.89 ml.) over 2 minutes. The mixture was evaporated to dryness and the residue, t-butyl 3-acetoxymethyl-7-[2-(2,2-diethoxyethyl)-3-t-butyldimethylsilyl]guanidinoceph-3-em-4-carboxylate, was dissolved in acetonitrile (50 ml.) and the mixture treated first with 50% w/v aqueous HF (0.8 ml.) at room temperature for 15 minutes and then with 12N aqueous HCl (1.0 ml.) for 1.5 hours at room temperature. The reaction mixture was evaporated to dryness and the residue triturated with ether to give t-butyl 3-acetoxymethyl-7-(imidazol-2-yl)aminoceph-3-em-4-carboxylate as a mixture of salts. This powder was dissolved in TFA (5 ml.) and this solution allowed to stand for 15 minutes at room temperature. The solvent was evaporated and the residue triturated with ether (yield from 7-amino derivative 41%) and then purified by chromatography on "Dowex" 1 resin (acetate form) using 0.1% v/v aqueous HOAc as eluant to give 3-acetoxymethyl-7-(imidazol-2-yl)aminoceph-3-em-4-carboxylic acid (yield from 7-amino derivaive 34%) having the following n.m.r. in $d_6DMSO$: 2.1 (s, 3H); 3.45 (d, 1H); 3.7 (d, 1H); 4.8 (d, 1H); 5.15 (d, 1H); 5.3 (d, 1H); 5.7 (d, 1H); 7.1 (s, 2H); 9.4 (d, 1H).

The 1-(2,2-diethoxyethyl)-3-t-butyldimethylsilylcarbodiimide used as starting material may be obtained by repeating the last part of Example 1 using t-butyldimethylsilyl chloride in place of trimethylsilyl chloride. The product was not distilled, and had the following n.m.r. in $CCl_4$: 0.25 (s, 6H); 1.05 (s, 9H); 1.3 (t, 6H); 3.25 (d, 2H); 3.4–3.9 (m, 4H); 4.55 (t, 1H).

EXAMPLE 3

To a suspension of 3-acetoxymethyl-7-aminoceph-3-em-4-carboxylic acid (136 mg.) in $CH_2Cl_2$ (10 ml.) was added N-trimethylsilyl-1-trimethylsilyloxyvinylamine (122 μl.) and the mixture was stirred at room temperature for 2 hours to give a solution of the trimethylsilyl ester. To this solution was added 1-(2,2-diethoxyethyl)-3-t-butyldimethylsilylcarbodiimide (150 mg.), then a solution of trifluoromethanesulphonic acid (45 μl.) in dry $CH_2Cl_2$ (1 ml.), and the mixture stirred for 5 minutes and then evaporated to dryness. The residue, trimethylsilyl 3-acetoxymethyl-7-[2-(2,2-diethoxyethyl)-3-t-butyldimethylsilyl]-guanidinoceph-3-em-4-carboxylate, was dissolved in acetonitrile (5 ml.) and to this solutin was added 50% w/v aqueous HF (40 μl.) and 12N aqueous HCl (40 μl.). After 4 hours at ambient temperature the pH of the mixture was adjusted to 4 with aqueous NaHCO$_3$ and the mixture allowed to stand for 18 hours. The solvent was evaporated to dryness (yield from 7-amino derivative 53%) and the product purified to give 3-acetoxymethyl-7-(imidazol-2-yl)aminoceph-3-em-4-carboxylic acid having the same n.m.r. as the product of Example 2.

EXAMPLE 4

The process described in Example 1 was repeated using 3-acetoxymethyl-7-aminoceph-3-em-4-carboxylic acid as starting material. There was thus obtained 3-acetoxymethyl-7-(imidazol-2-yl)aminoceph-3-em-4-carboxylic acid (yield from 7-amino derivative 50%) identical to the product obtained in Example 2.

EXAMPLE 5

To a stirred solution of t-butyl 3-acetoxymethyl-7-aminoceph-3-em-4-carboxylate (164 mg.) in anhydrous CH$_2$Cl$_2$ at room temperature was added a molar solution of anhydrous toluene-p-sulphonic acid in CH$_2$Cl$_2$ (0.5 ml.) and then 1-(2,2-diethoxyethyl)-3-trimethylsilylcarbodiimide (125 μl.). Stirring was continued for 10 minutes and the solvent was evaporated. The residue, t-butyl 3-acetoxymethyl-7-[2-(2,2-diethoxyethyl)-3-trimethylsilyl]guanidinoceph-3-em-4-carboxylate, was dissolved in acetonitrile and 12N aqueous HCl (42 μl.) added. The mixture was stirred for 1.5 hours at room temperature, and the solvent evaporated. To the residue, t-butyl 3-acetoxymethyl-7-(imidazol-2 -yl)aminoceph-3-em-4-carboxylate, was added trifluoroacetic acid and the mixture was stirred for 15 minutes. The solvent was evaporated and the residue was precipitated from a solution in the minimum of CH$_2$Cl$_2$ with ether. The precipitate was dissolved in CH$_2$Cl$_2$/MeOH and the solvent evaporated to give 3-acetoxymethyl-7-(imidazol-2-yl)aminoceph-3-em-4-carboxylic acid (262 mg. of 42% strength), identical with the product obtained in Example 2 (yield from 7-amino derivative 65%).

EXAMPLE 6

The process described in Example 5 was repeated, using the cephalosporin diphenylmethyl ester in place of the corresponding t-butyl ester, to give the same product (yield from 7-amino derivative 62%).

EXAMPLE 7

A mixture of t-butyl 7-amino-3-methylceph-3-em-4-carboxylate hydrochloride (306 mg.) and 1-(2,2-diethoxyethyl)-3-methoxymethylcarbodiimide (200 mg.) in acetonitrile (15 ml.) was stirred until the hydrochloride salt went into solution (30 minutes). There was thus obtained a solution of t-butyl 7-[2-(2,2-diethoxyethyl)-3-methoxymethyl]guanidino-3-methylceph-3-em-4-carboxylate to which was added 2N aqueous HCl (1.5 ml.), and the mixture was allowed to stand for 18 hours. The solvent was evaporated and the residue was purified by chromatography on silica using CH$_2$Cl$_2$/MeOH/HOAc 96:4:2 v/v/v as eluant to give t-butyl 7-(5-hydroxy-1-methoxymethylimidazolin-2-yl)amino-3-methylceph-3-em-4-carboxylate as a mixture of diasteroisomers. A solution of this product (20 mg.) in DMF (1.0 ml.) was heated at 90° for 15 minutes. The solvent was evaporated and the residue was purified by preparative thin layer chromatography on silica using CH$_2$Cl$_2$/MeOH/HOAc 85:15:5 v/v/v as eluant. There was thus obtained t-butyl 3-methyl-7-imidazol-2-yl)aminoceph-3-em-4-carboxylate (2 mg.) and t-butyl 3-methyl-7-(1-methoxymethylimidazol-2-yl)aminoceph-3-em-4-carboxylate (3 mg.). These products were separately treated with trifluoroacetic acid to give the corresponding acids. The 3-methyl-7-(imidazol-2-yl)aminoceph-3-em-4-carboxylic acid had the following n.m.r. in d$_6$DMSO: 2.075 (s, 3H); 3.48 (dd, 2H); 5.13 (d, 1H); 5.5 (q, 1H); 7.07 (s, 2H); 9.45 (d, 1H).

The 1-(2,2-diethoxyethyl)-3-methoxymethylcarbodiimide used as starting material may be obtained as follows:

To a solution of sodium isothiocyanate (23.4 g.) in acetone (100 ml.) was dropwise added chloromethylmethyl ether (16 ml.). After 15 minutes the suspension was filtered, the filtrate evaporated and the residue taken up in ether. This solution was filtered and the filtrate evaporated to dryness to give methoxymethylisothiocyanate (11 g.) which was used without further purification.

To a solution of this isothiocyanate (8 g.) in CH$_2$Cl$_2$ (100 ml.) was dropwise added a solution of 2,2-diethoxyethylamine (11.6 ml.) in CH$_2$Cl$_2$ (100 ml.) with stirring at room temperature. After 1 hour the solvent was evaporaged and the residue purified by chromatography on silica gel (200 g.) using CH$_2$Cl$_2$/MeOH 95:5 v/v as eluant. There was thus obtained 1-(2,2-diethoxyethyl)-3-methoxymethylthiourea (16 g.) as an oil which crystallised.

A mixture of the above thiourea (16 g.), mercuric oxide (58 g.) and sulphur (20 mg.) in acetone (200 ml.) was heated under reflux with stirring for 1.5 hours. The suspension was filtered through a pad of MgSO$_4$ and the filtrate was evaporated. The residue was purified by short path distillation at 170° and 0.2 mm to give 1-(2,2-diethoxyethyl)-3-methoxymethylcarbodiimide (8.5 g.) having the following n.m.r. in CDCl$_3$: 1.2 (t, 6H); 3.2-3.8 (m, 8H); 3.4 (s, 3H); 4.55 (t, 1H); 4.65 (s, 2H).

EXAMPLE 8

To a solution of t-butyl 7-amino-3-methylceph-3-em-4-carboxylate (810 mg.) and 1-(2,2-diethoxyethyl)-3-(tetrahydropyran-2-yl)carbodiimide (726 mg.) in dry CH$_2$Cl$_2$ (8 ml.) under nitrogen at room temperature was dropwise added a 2N ether solution of HCl (1.5 ml.) in CH$_2$Cl$_2$ (4 ml.) over 30 minutes. The mixture was allowed to stand for a further 30 minutes and then evaporated to dryness. To a solution of the residue, t-butyl 7-[2-(2,2-diethoxyethyl)-3-(tetrahydropyran-2-yl)guanidino]-3-methylceph-3-em-4-carboxylate (1.7 g.) in acetonitrile (8 ml.) was added 3N aqueous HCl (1 ml.) and the mixture was heated at 50° for 2 hours, then evaporated to dryness at 30°. The residue was purified by chromatography on silica gel using CH$_2$Cl$_2$/MeOH/HOAc 89:10:1 v/v/v as eluant to give, after precipitation from CH$_2$Cl$_2$ solution will ether, t-butyl 3-methyl-7-[5-hydroxy-1-(tetrahydropyran-2-yl)imidazolin-2-yl]aminoceph-3-em-4-carboxylate (900 mg.) as a mixture of diastereoisomers. A solution of this product in trifluoroacetic anhydride was allowed to stand at room temperature under nitrogen for 6 hours, and then evaporated to dryness. The residue was purified by chromatography on silica to give t-butyl 3-methyl-7-(imidazol-2-yl)aminoceph-3-em-4-carboxylate. This compound was treated with trifluoroacetic acid to give the free acid, identical to the product obtained in Example 7.

The 1-(2,2-diethoxyethyl)-3-(tetrahydropyran-2-yl)carbodiimide used as starting material may be prepared as follows:

To a solution of dihydropyran (17.64 g.) in benzene (50 ml.) was dropwise added with cooling a solution of isothiocyanic acid in benzene (0.21 mole in 100 ml.). The mixture was allowed to stand at room temperature for 1 hour, filtered, and the filtrate evaporates to dryness to give tetrahydropyran-2-isothiocyanate as a yellow oil (30 g.).

A solution of this oil (4.4 g.) in ether (40 ml.) was added with stirring and cooling under nitrogen to a solution of aminoacetaldehyde diethyl acetal (4.4 ml.) in ether (40 ml.). The mixture was allowed to stand at room temperature for 1 hour then washed with water (×2), dried (MgSO$_4$) and the solvent evaporated. The residue was triturated with petroleum ether (b.p. 40°–60°) to give 1-(2,2-diethoxyethyl)-3-tetrahydropyran-2-yl)thiourea (7.5 g.), m.p. 61°–62°.

To a solution of this thiourea (4.6 g.) in benzene (100 ml.) was added with stirring mercuric oxide (14.43 g.) and sulphur (100 mg.). The mixture was heated for 15 hours, cooled and filtered, and the filtrate evaporated to dryness to give 1-(2,2-diethoxyethyl)-3-tetrahydropyran-2-yl)carbodimide which was used without further purification.

EXAMPLE 9

To a stirred mixture of 7-amino-3-acetoxymethyl-ceph-3-em-4-carboxylic acid (5.44 g.) and acetonitrile (25 ml.) under argon at ambient temperature (22°–24°) was added N-trimethylsilyl-1-trimethylsilyloxyvinylamine (4.93 ml.) over 2 minutes and the mixture stirred at ambient temperatures for 2.5 hours to give a clear orange solution. To this solution, cooled in ice, was added 1-(2,2-diethoxyethyl)-3-trimethylsilylcarbodiimide (4.6 g.) over 2 minutes, followed by conc. sulphuric acid (1.06 ml.) over 13 minutes, the temperature of the reaction mixture being maintained below 7°. The solution temperature was maintained at 0° for 30 minutes, then more 1-(2,2-diethoxyethyl)-3-trimethylsilylcarbodiimide (0.46 g.) and more conc. sulphuric acid (95 l.) were added, the temperature of the reaction mixture being maintained below 3°. After another 30 minutes at 0° further additions of the same amount of these reagents were made. The golden yellow solution was maintained at 0° for 1 hour and then (for convenience) stored at −20° under argon for 2 days. To this solution of trimethylsilyl 3-acetoxymethyl-7-[2-(2,2-diethoxyethyl)-3-trimethylsilyl]guanidinoceph-3-em-4-carboxylate stirred in an ice bath was added boron trifluoride acetic acid complex (40% w/w; 7.3 ml.) over 6 minutes, the temperature of the reaction mixture being maintained below 5°. The temperature of the solution was maintained at 0°–1° for 7.5 hours and then (for convenience) stored at −20° under argon for 18 hours. The solution was diluted with ice-cold water (100 ml.), the temperature of the mixture being maintained below 5° and then extracted with cold dichloromethane (60 ml.; 2×40 ml.). The aqueous layer was diluted with more ice-cold water (100 ml.) and the pH adjusted to 4 with 9N aqueous sodium hydroxide solution (10 ml.). The solution was applied to a column of Diaion HP-20 resin (160 ml. bed volume) made up in deionised water. The resin was washed with water (160 ml.) and then the product was eluted with acetonitrile/water 20:80 v/v. The fraction (ca. 110 ml.) rich in product was allowed to stand for 1 hour at room temperature whereupon the product cyrstallised out as finse colourless needles. The mixture was stored at 0° for 2 days and the solid was filtered off, washed with cold acetonitrile (2×5 ml.) and dried in vacuo to give 3-acetoxymethyl-7-(imidazol-2-yl)aminoceph-3-em-4-carboxylic acid (3.94 g.) having the following analysis: strength (HPLC comparison with an authentic sample of known strength) 88.5%, water content 9.7%.

EXAMPLE 10

The process described in Example 4, 5 or 6 may be repeated, using an equivalent amount of the trimethylsilyl, t-butyl or diphenylmethyl ester of the appropriate 3-substituted 7-aminoceph-3-em-4-carboxylic acid in place of the corresponding ester of 3-acetoxymethyl-7-aminoceph-3-em-4-carboxylic acid to give the following compounds.

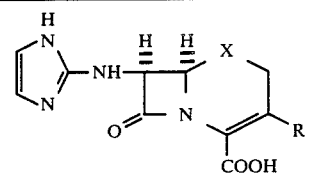

| R | X | Footnotes |
|---|---|---|
| CH$_2$S—\<triazole, N—N / N—N, substituent CH$_2$CH$_2$N(CH$_3$)$_2$\> | S | 1 |
| CH$_2$S—\<triazole, N—N / N—N, substituent CH$_3$\> | S | 2 |
| CH$_2$S—\<thiadiazole, N—N / S, substituent CH$_3$\> | S | 3 |
| CH$_2$S—\<phenyl with COOH ortho\> | S | 4 |
| CH$_2$S—\<triazole, N—N / N—N, substituent CH$_2$COOH\> | S | 5 |
| CH$_3$S—\<thiadiazole, N—N / S\> | S | 6 |

| | | |
|---|---|---|
| 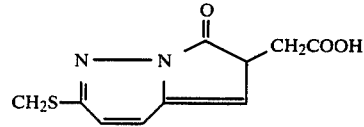 | S | 7 |
| 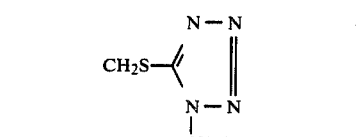 | S | 8 |
| 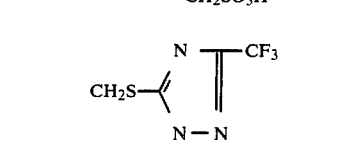 | S | 9 |
| 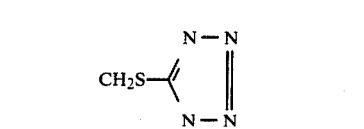 | S | 10 |
| 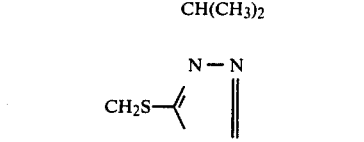 | S | 11 |
| 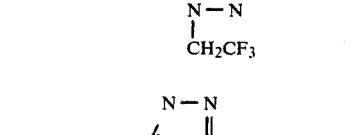 | S | 12 |
| 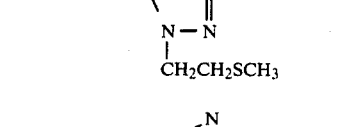 | S | 13 |
| 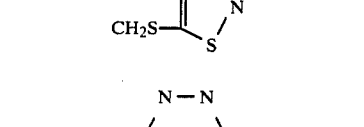 | S | 14 |
| CH$_2$OCH$_3$ | S | 15 |
| CH$_2$OCOPh | S | 16 |
| H | S | 17 |
| 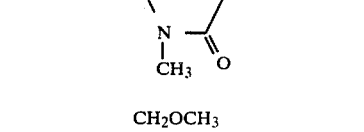 | S | 18 |
| 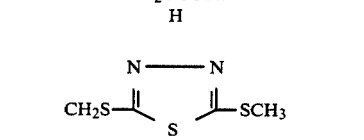 | S | 19 |
| CH$_2$N$_3$ | S | 20 |
| CH$_2$NH$_2$ | S | 21 |
| CH$_2$NHCOCH$_3$ | S | 22 |
| Cl | S | 23 |
| 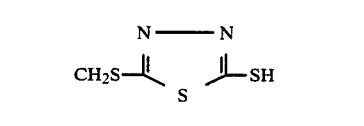 | S | 24 |
| 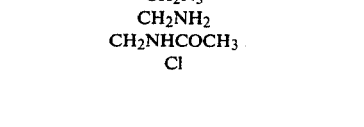 | S | 25 |
|  | S | 26 |
| 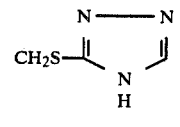 | S | 27 |
| 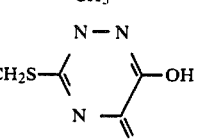 | S | 28 |
| 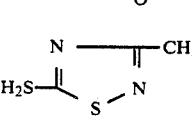 | S | 29 |
| CH$_2$OH | S | 30 |
| CH$_2$OCONH$_2$ | S | 31 |
| 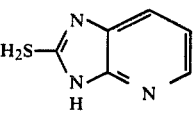 | S | 32 |
| 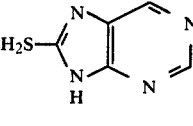 | S | 33 |
| 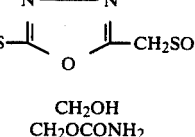 | S | 34 |
| 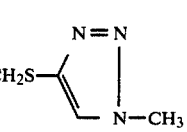 | S | 35 |
| 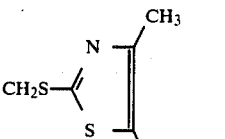 | S | 36 |
| CH$_2$OCOCH$_3$ | S—O | 37 |
| Cl | S—O | 38 |

| | | |
|---|---|---|
| CH₂OCOCH₃ | S—O | 39 |

Footnotes
1. n.m.r. in D₂O:- 3.1 (s, 6H); 3.6–4.0 (m, 4H); 4.2 (m, 2H); 4.9 (m, 2H); 5.3–5.5 (2d, 2H); 6.9 (s, 2H).
2. m.p. 120–125° and n.m.r. in d₆DMSO:- 3.7 (m, 2H); 3.9 (s, 3H); 4.3 (m, 2H); 5.15 (d, 1H); 5.5 (dd, 1H); 7.0 (s, 2H); 9.4 (d, 1H).
3. m.p. 140–145° and n.m.r. in d₆DMSO:- 2.6 (s, 3H); 3.4 (d, 1H); 3.8 (d, 1H); 4.2 (d, 1H); 4.5 (d, 1H); 5.1 (d, 1H); 5.5 (dd, 1H); 6.9 (s, 2H); 9.2 (s, 1H).
4. m.p. 175–180° and n.m.r. in d₆DMSO + CD₃COOD:- 3.5 (d, 1H); 3.8 (d, 1H); 4.0 (d, 1H); 4.3 (d, 1H); 5.2 (d, 1H); 5.6 (d, 1H); 7.0 (s, 2H); 7.2–8.0 (m, 3H).
5. n.m.r. in CD₃OD + D₂O:- 3.65 (d, 1H); 3.9 (d, 1H); 4.3 (d, 1H); 4.5 (d, 1H); 5.25 (d, 1H); 5.25 (s, 1H); 5.5 (dd, 1H); 7.0 (s, 2H).
6. n.m.r. in d₆DMSO + CD₃COOD:- 3.52 (d, 1H); 3.79 (d, 1H); 4.33 (d, 1H); 4.6 (d, 1H); 5.12 (d, 1H); 5.58 (d, 1H); 6.83 (s, 2H); 9.49 (s, 1H).
7. n.m.r. of dihydrate in D₂O + TFA:- 3.3 (d, 1H); 3.64 (d, 1H); 3.92 (d, 1H); 4.26 (d, 1H); 4.59 (s, 2H); 4.93 (d, 1H); 5.2 (d, 1H); 6.56 (s, 2H); 6.75 (d, 1H); 7.25 (d, 1H).
8. n.m.r. of toluene-p-sulphonate in d₆DMSO + CD₃COOD:- 2.32 (s, 3H); 3.64 (d, 1H); 3.9 (d, 1H); 4.19 (d, 1H); 4.46 (d, 1H); 5.05 (s, 2H); 5.17 (d, 1H); 5.57 (d, 1H); 7.06 (s, 2H); 7.14 (d, 2H); 7.54 (d, 2H).
9. m.p. 244°; n.m.r. in D₂O + TFA:- 3.03 (d, 1H); 3.32 (d, 1H); 3.58 (d, 1H); 3.78 (d, 1H); 4.95 (d, 1H); 6.32 (s, 2H).
10. hydrate, m.p. 219–220° (decomp.) and n.m.r. in D₂O + TFA:- 1.5 (d, 6H); 3.6 (d, 1H); 3.83 (d, 1H); 4.2 (s, 2H); 4.6–5.1 (m, 1H); 5.48 (d, 1H); 6.82 (s, 2H).
11. n.m.r. in D₂O + TFA:- 3.35 (d, 1H); 3.6 (d, 1H); 4.14 (s, 2H); 4.98 (d, 1H); 5.0 (q, 2H); 5.26 (d, 1H); 6.64 (s, 2H).
12. n.m.r. in d₆DMSO + CD₃COOD:- 2.05 (s, 3H); 2.97 (t, 2H); 3.52 (d, 1H); 3.78 (d, 1H); 4.36 (bs, 2H); 4.51 (t, 2H); 5.09 (d, 1H); 5.52 (d, 12H); 6.82 (s, 2H).
13. n.m.r. in d₆DMSO + CD₃COOD:- 3.47 (d, 1H): 3.71 (d, 1H); 4.36 (s, 2H); 5.13 (d, 1H); 5.58 (d, 1H); 6.81 (s, 2H); 8.88 (s, 1H).
14. n.m.r. in d₆DMSO:- 3.3 (s, 3H); 3.5 (d, 1H); 3.8 (d, 1H); 3.9 (d, 1H); 4.3 (d, 1H); 5.2 (d, 1H); 5.7 (m, 1H); 6.9 (s, 2H).
15. n.m.r. of TFA salt in d₆DMSO:- 3.2 (s, 3H); 3.5 (m, 2H); 4.2 (s, 2H); 5.2 (d, 1H); 5.5 (d, 1H); 6.9 (d, 2H).
16. n.m.r. of TFA salt in d₆DMSO + CD₃CO₂D:- 3.6 (d, 1H); 3.9 (d, 1H); 5.0 (d, 1H); 5.3 (d, 1H); 5.4 (d, 1H); 5.7 (d, 1H); 7.0 (d, 2H); 7.4–8.1 (m, 5H).
17. n.m.r. of TFA salt of d₆DMSO + CD₃COOD:- 3.65 (s, 2H); 5.1 (d, 1H); 5.7 (d, 1H); 6.55 (t, 1H); 7.0 (s, 2H).
18. n.m.r. of TFA salt in d₆DMSO + CD₃COOD:- 2.8 (s, 3H); 3.7 (d, 1H); 3.8 (d, 1H); 4.3 (d, 1H); 4.5 (d, 1H); 5.2 (d, 1H); 7.0 (s, 2H).
19. n.m.r. of TFA salt in d₆DMSO + CD₃COOD:- 3.5 (d, 1H); 3.6 (d, 1H); 4.1 (d, 1H); 4.2 (d, 1H); 5.05 (d, 1H); 5.6 (d, 1H); 6.8 (s, 2H).
20. n.m.r. of TFA salt containing 20% of the delta-2 isomer in d₆DMSO + CD₃CO₂D:- 3.55 (d, 1H); 3.75 (d, 1H); 4.0 (d, 1H); 4.5 (d, 1H); 5.25 (d, 1H); 5.75 (d, 1H); 7.0 (s, 2H).
21. n.m.r. of ditrifluoroacetate containing 30% of delta-2 isomer in d₆DMSO + CD₃COOD:- 3.2–3.8 (m, 4H); 5.05 (d, 1H); 5.55 (d, 1H); 6.9 (s, 2H).
22. n.m.r. in d₆DMSO + CD₃COOD:- 1.9 (s, 3H); 3.3 (d, 1H); 3.55 (d, 1H); 3.9 (d, 1H); 4.2 (d, 1H); 5.05 (d, 1H); 5.5 (d, 1H); 6.8 (s, 2H); 8.2 (s, 3H).
23. n.m.r. of HCl salt in TFA:- 3.6 (d, 1H); 3.9 (d, 1H); 5.4 (s, 1H); 5.6 (s, 1H); 6.85 (s, 2H).
24. n.m.r. of HCl salt in d₆DMSO:- 3.8 (s, 2H); 4.35 (q, 2H); 5.15 (q, 2H); 7.08 (s, 2H); 9.11 (s, 1H).
25. n.m.r. in d₆DMSO + TFA:- 3.2 (d, 1H); 3.6 (d, 1H); 3.7 (s, 3H); 3.7 (d, 1H); 4.1 (d, 1H); 5.25 (d, 1H); 5.51 (d, 1H); 7.05 (s, 2H).
26. n.m.r. in d₆DMSO + TFA:- 2.65 (s, 3H); 3.45–4.0 (m, 2H); 4.5 (s, 2H); 5.25 (d, 1H); 5.6 (d, 1H); 6.9 (s, 2H).
27. n.m.r. in d₆DMSO:- 3.6 (s, 2H); 3.8–4.1 (m, 2H); 5.05 (d, 1H); 5.45 (d, 1H); 6.8 (s, 2H); 6.8–8.1 (m, 3H).
28. n.m.r. in D₂O + TFA:- 3.95 (d, 1H); 4.22 (d, 1H); 5.0 (br, 2H); 5.52 (d, 1H); 5.8 (d, 1H); 7.2 (s, 2H); 9.0–9.3 (m, 2H).
29. n.m.r. in d₆DMSO/HOAc:- 3.35–3.85 (m, 2H), 3.65–4.15 (m, 2H); 4.0 (s, 2H); 5.2 (d, 1H); 5.35 (br, 1H); 7.0 (s, 2H).
30. n.m.r. in D₂O + pyridine:- 3.34 (d, 1H); 3.65 (d, 1H); 4.25 (d, 1H); 4.5 (d, 1H); 5.26 (d, 1H); 5.55 (d, 1H); 6.65 (d, 2H).
31. n.m.r. in d₆DMSO + CD₃COOD:- 3.56 (q, 2H); 4.8 (q, 2H); 5.18 (d, 1H); 5.58 (d, 1H); 6.96 (s, 1H).
32. n.m.r. in d₆DMSO + CD₃COOD:- 3.46 (d, 1H); 3.74 (d, 1H); 3.86 (d, 1H); 4.09 (s, 3H); 4.17 (d, 1H); 5.08 (d, 1H); 5.5 (d, 1H); 6.84 (s, 2H); 8.69 (s, 1H).
33. n.m.r. in d₆DMSO + CD₃COOD:- 1.71 (m, 2H); 2.18 (t, 2H); 2.24 (s, 3H); 2.7 (t, 3H); 3.44 (d, 1H); 3.73 (d, 1H); 4.07 (d, 1H); 4.47 (d, 1H); 5.06 (d, 1H); 5.54 (d, 1H); 6.8 (s, 2H).
34. n.m.r. in d₆DMSO + CD₃COOD:- 3.46 (d, 1H); 3.73 (d, 1H); 4.17 (s, 2H); 5.16 (d, 1H); 5.55 (d, 1H); 6.8 (s, 2H); 8.28 (dd, 1H); 7.05–7.69 (3H).
35. n.m.r. in d₆DMSO + CD₃COOD:- 2.13 (s, 3H); 3.41 (d, 1H); 3.73 (d, 1H); 4.19 (d, 1H); 4.44 (d, 1H); 5.06 (d, 1H); 5.54 (d, 1H); 6.71 (s, 2H).
36. n.m.r. in d₆DMSO + CD₃COOD:- 3.62 (m, 2H); 3.9 (s, 3H); 5.1 (d, 1H); 5.5 (d, 1H); 6.7 (d, 1H); 7.2 (d, 1H); 6.75 (s, 2H).
37. S—O in β configuration; n.m.r. of trifluoroacetate salt in CD₃COOD:- 2.0 (s, 3H); 3.44 (d, 1H); 3.97 (d, 1H); 4.65 (d, 1H); 4.95 (d, 1H); 5.23 (d, 1H); 5.8 (d, 1H); 6.87 (s, 2H).
38. mixture of α and β isomers at the 1-position; n.m.r. in d₆DMSO + TFA:- 4.0 (s, 1H); 4.15 (s, 1H); 4.95 and 5.1 (d, 1H); 5.7 and 5.8 (d, 1H); 7.05 (s, 2H).
39. S—O in α configuration; n.m.r. of toluene-p-sulphonate salt in d₆DMSO + CD₃COOD:- 2.05 (s, 3H); 2.28 (s, 3H); 3.75 (m, 2H); 4.65 (d, 1H); 5.05 (d, 1H); 5.05 (d, 1H); 5.7 (d, 1H); 7.08 (s, 2H); 7.3 (q, 4H).

FORMULAE

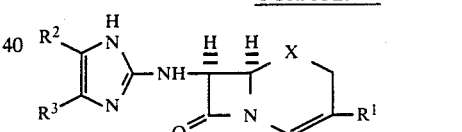

I

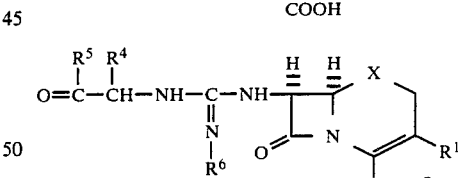

II

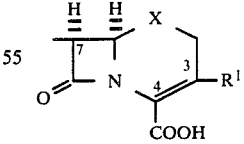

III

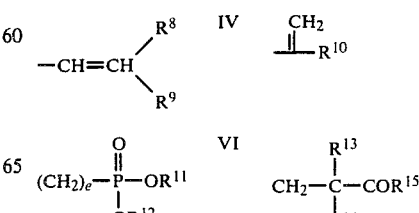

IV   V

VI   VII

-continued
FORMULAE

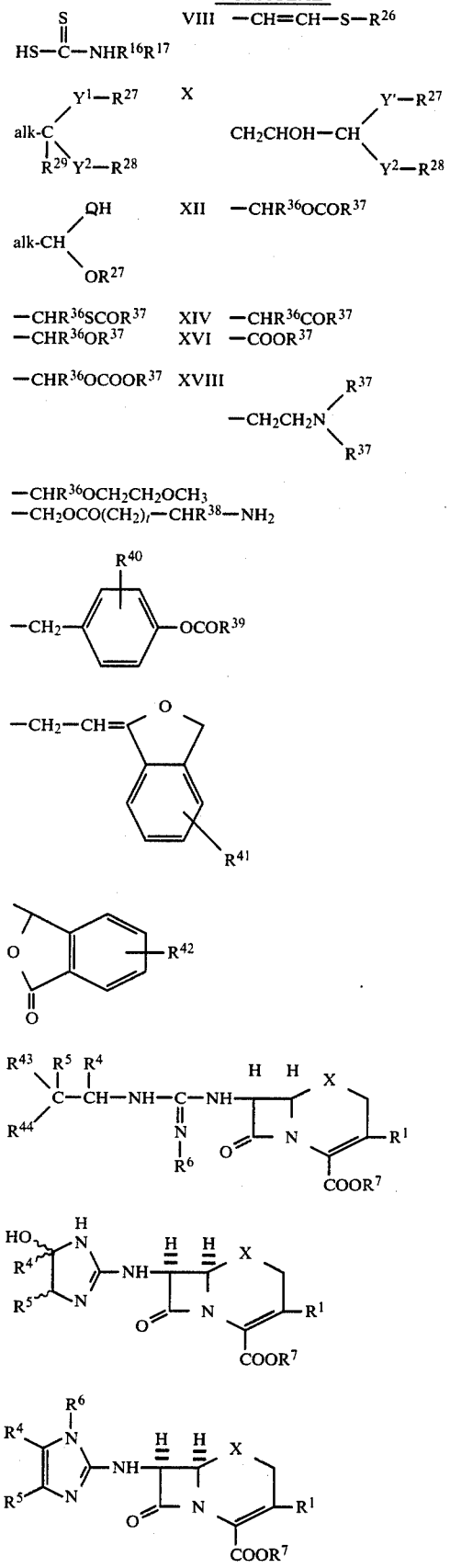

-continued
FORMULAE

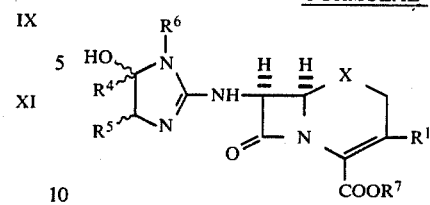  IX

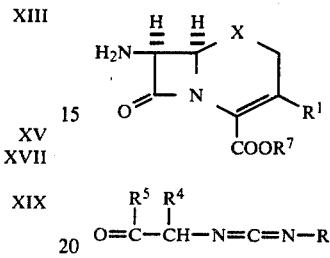  XIII

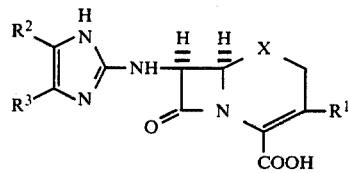  XIX $$O=\overset{R^5}{\underset{|}{C}}-\overset{R^4}{\underset{|}{CH}}-N=C=N-R^6$$  XXX

We claim:

1. A process for the manufacture of a cephalosporin derivative of the formula I:

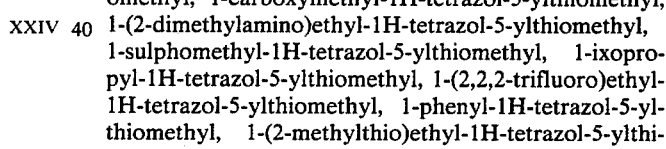

wherein X is sulphur; R¹ is hydrogen, chlorine, methyl, acetoxymethyl, methoxymethyl, hydroxymethyl, azidomethyl, aminomethyl, benzoyloxymethyl, acetylaminomethyl, carbamoyloxymethyl, 2-(1-methyltetrazol-5-ylthio)-transvinyl, 1-methyl-1H-tetrazol-5-ylthiomethyl, 1-carboxymethyl-1H-tetrazol-5-ylthiomethyl, 1-(2-dimethylamino)ethyl-1H-tetrazol-5-ylthiomethyl, 1-sulphomethyl-1H-tetrazol-5-ylthiomethyl, 1-ixopropyl-1H-tetrazol-5-ylthiomethyl, 1-(2,2,2-trifluoro)ethyl-1H-tetrazol-5-ylthiomethyl, 1-phenyl-1H-tetrazol-5-ylthiomethyl, 1-(2-methylthio)ethyl-1H-tetrazol-5-ylthiomethyl, 1,3,4-thiadiazol-2-ylthiomethyl, 5-methyl-1,3,4-thiadiazol-2-ylthiomethyl, 1,2,3-thiadiazol-5-ylthiomethyl, 1H-1,2,3-triazol-4-ylthiomethyl, 5-trifluoromethyl-1H-1,2,4-triazol-3-ylthiomethyl, 4,6-dimethylpyrimid-2-ylthiomethyl, 2-thiazolin-2-ylthiomethyl, benzoxazol-2-ylthiomethyl, benzthiazol-2-ylthiomethyl, 2-carboxyphenylthiomethyl, (6-carboxymethyl-7-hydroxypyrrolo[1,2-b]pyridazin-2-yl)thiomethyl, 2-methylthio-1,3,4-thiadiazol-5-ylthiomethyl, 2-mercapto-1,3,4-thiadiazol-5-ylthiomethyl, 2-acetylamino-1,3,4-thiadiazol-5-ylthiomethyl, 5-methyl-1,2,4-thiadiazol-2-ylthiomethyl, 2-sulphomethyl-1,2,4-oxadiazol-5-ylthiomethyl, 4-methyl-5-(3-carboxypropyl)thiazol-2-ylthiomethyl, 2H-2-methyl-1,2,3-triazol-4-ylthiomethyl, 1H-1,2,4-triazol-2-ylthiomethyl, 4,5-dihydro-6-hydroxy-4-methyl-5-oxo-1,2,4-triazin-3-ylthiomethyl, 2,5-dihydro-6-hydroxy-2-methyl-5-oxo-1,2,4-triazin-3-ylthiomethyl, 1-oxidopyrid-2-ylthiomethyl, imidazo[4,5-b]pyrid-2-ylthiomethyl or imidazo[4,5-d]pyrimidin-2-ylthiomethyl R² is hydrogen; R³ is hydrogen; and the pharmaceutically-acceptable acid-addition and base-addition salts thereof, characterised by cyclisation of a compound of the formula XXV:

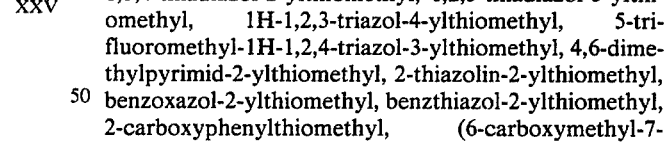

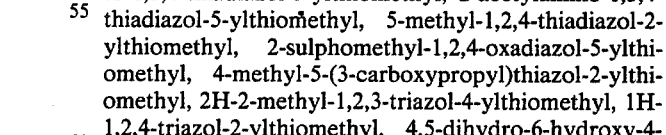

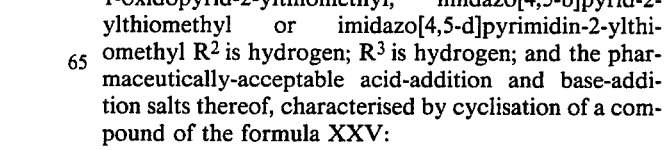

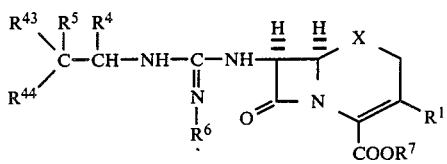 XXV or an acid-addition salt thereof, in which X and $R^1$ have the meanings stated above, $R^4$ and $R^5$ individually have one of the values given above for $R^2$ and $R^3$, $R^6$ is a nitrogen-protecting group selected from a group of the formula $SiR^{30}R^{31}R^{32}$ or $CH_2OSiR^{30}R^{31}R^{32}$ in which $R^{30}$, $R^{31}$, and $R^{32}$, same or different, are 1–6C alkyl, phenyl or benzyl, of the formula $CH_2OR^{33}$ in which $R^3$ is 1–6C alkyl, or $R^6$ is triphenylmethyl, tetrahydropyran-2-yl or tetrahydropyran-2-yloxymethyl; $R^7$ is hydrogen, t-butyl, diphenylmethyl, p-methoxybenzyl, benzyl, p-nitrobenzyl or 2,2,2-trichloroethyl or $R^7$ is trisubstituted silyl in which the substituents are selected from 1–6C alkyl, phenyl and substituted phenyl, or $R^7$ is of the formula XIII to XXIV inclusive:

| | |
|---|---|
| $-CHR^{36}OCOR^{37}$ | XIII |
| $-CHR^{36}SCOR^{37}$ | XIV |
| $-CHR^{36}COR^{37}$ | XV |
| $-CHR^{36}OR^{37}$ | XVI |
| $-COOR^{37}$ | XVII |
| $-CHR^{36}OCOR^{37}$ | XVIII |

 XIX

| | |
|---|---|
| $-CHR^{36}OCH_2CH_2OCH_3$ | XX |
| $-CH_2OCO(CH_2)_t-CHR^{38}-NH_2$ | XXI |

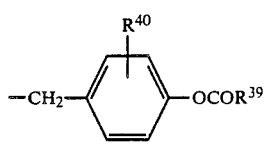 XXII

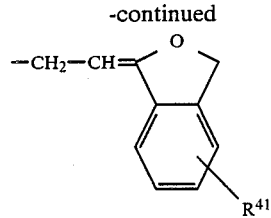 XXIII

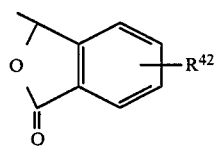 XXIV in which $R^{36}$ is hydrogen or 1–6C alkyl, $R^{37}$ is 1–6C alkyl, $R^{38}$ is hydrogen, 1–6C alkyl, phenyl(1–6C)alkyl or 2–6C alkoxycarbonyl, t is 0 to 1, $R^{39}$ is 1–6C alkyl, phenyl or phenyl(1–6C)alkyl, $R^{40}$ is hydrogen or one, two or three radicals selected from halogen, nitro, cyano, 1–6C alkyl, 1–6C alkoxy, 1–6C alkylthio, 1–6C alkylsulphinyl, 1–6C alkanesulphonyl, 2–6C alkoxycarbonyl, 2–6C alkoxythiocarbonyl, 2–6C alkanoylamino, phenyl, phenoxy, phenylthio, phenylsulphinyl, phenylsulphonyl, phenoxycarbonyl, phenylthiocarbonyl, and phenoxythiocarbonyl, $R^{41}$ is hydrogen or one of the values for $R^{39}$ given above and $R^{42}$ is hydrogen or one, two or three radicals selected from halogen, 1–6C alkyl and 1–6C alkoxy; $R^{43}$ and $R^{44}$, same or different, are hydroxy, cyano or of the formula $NR^{45}R^{46}$ in which $R^{45}$ and $R^{46}$ are 1–6C alkyl or phenyl or are joined to form a ring or of the formula $OSiR^{47}R^{48}R^{49}$ in which $R^{47}$, $R^{48}$ and $R^{49}$, same or different, are 1–6C alkyl, phenyl(1–6C)alkyl, or phenyl or $R^{43}$ and $R^{44}$ together are of the formula $R^{50}-ON=$ in which $R^{50}$ is 1–6C alkyl or hydroxy or of the formula $R^{51}R^{52}NN=$ in which $R^{51}$ and $R^{52}$ are 1–6C alkyl or phenyl, or $R^{43}$ is hydrogen and $R^{44}$ is nitro, or $R^{43}$ and $R^{44}$ are of the formula $A-R^{53}$ and $B-R^{54}$ respectively in which A and B are oxygen, sulphur, sulphinyl or NH and $R^{53}$ and $R^{54}$ are joined to form an ethylene or propylene chain which is optionally substituted by one or two 1–6C alkyls, or when A and B are oxygen, sulphur or sulphinyl, $R^{53}$ and $R^{54}$, same or different, are 1–6C alkyl, 1–6C alkanoyl, phenyl, or phenyl(1–6C)alkyl, thereafter, when $R^7$ is a substituent other than hydrogen, replacing said substituent with $R^7$ and thereafter, when the compound of formula I is obtained in the form of the free base or salt, and a pharmaceutically-acceptable salt or free base respectively is required, converting said base or salt to the salt or base.

2. The process of claim 1 wherein $R^1$ is 1H-1,2,3-triazol-4-ylthiomethyl or acetoxymethyl, $R^6$ and $R^7$ are trimethylsilyl and $R^{43}$ and $R^{44}$ are ethoxy.

* * * * *